US009420780B2

(12) United States Patent
Vidal et al.

(10) Patent No.: US 9,420,780 B2
(45) Date of Patent: Aug. 23, 2016

(54) COMPOSITION, METHOD FOR PRODUCING THE COMPOSITION, AND PHYTOSANITARY FORMULATION CONTAINING SAME

(71) Applicant: RHODIA OPERATIONS, Aubersvilliers (FR)

(72) Inventors: Thierry Vidal, Lyons (FR); Benoit Abribat, Saint Fargeau Ponthierry (FR); Valerio Bramati, Arese (IT); Marc Balastre, Paris (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/350,599

(22) PCT Filed: Oct. 11, 2012

(86) PCT No.: PCT/EP2012/070172
§ 371 (c)(1),
(2) Date: Apr. 9, 2014

(87) PCT Pub. No.: WO2013/053834
PCT Pub. Date: Apr. 18, 2013

(65) Prior Publication Data
US 2014/0256554 A1   Sep. 11, 2014

(30) Foreign Application Priority Data
Oct. 13, 2011   (FR) .................................... 11 59258

(51) Int. Cl.
*A01N 25/02* (2006.01)
*A01N 25/04* (2006.01)

(52) U.S. Cl.
CPC ................ *A01N 25/02* (2013.01); *A01N 25/04* (2013.01)

(58) Field of Classification Search
CPC .............................. A01N 25/02; A01N 25/04
See application file for complete search history.

(56) References Cited

U.S. PATENT DOCUMENTS

| 4,506,051 A | 3/1985 | Rance |
| 8,735,324 B2 * | 5/2014 | Jentzer ................... A01N 25/02 504/358 |
| 8,981,148 B2 * | 3/2015 | Guglieri ............... C07C 231/02 106/287.25 |
| 9,090,538 B2 * | 7/2015 | Guglieri ................. A01N 25/02 |

(Continued)

FOREIGN PATENT DOCUMENTS

| FR | 2 926 699 A1 | 7/2009 |
| WO | 2009/092795 A1 | 7/2009 |

OTHER PUBLICATIONS

Anonymous, "Branched esteramides, diamides or mixtures thereof and their use as solvent in phytosanitary formulations"; Mar. 22, 2010; IP.com, IP.com No. IPCOM000194387D, pp. 1-37.*

(Continued)

*Primary Examiner* — Jane C Osowecki

(57) ABSTRACT

The present disclosure relates to compositions comprising from 10 to 90 wt % of a mixture M of compounds A having formula $R^1CONR^2R^3$, wherein $R^1$, $R^2$, and $R^3$ are described herein, and from 10 to 90 wt % of at least one compound B selected from the amide solvents, optionally combined with an ester solvent, and methods for producing the same. The present disclosure further relates to phytosanitary formulations comprising such compositions.

17 Claims, 1 Drawing Sheet

(56) References Cited

U.S. PATENT DOCUMENTS

2013/0210933 A1* 8/2013 Guglieri ............. A01N 25/02
514/785
2014/0221211 A1* 8/2014 Jentzer ............... A01N 25/02
504/301

OTHER PUBLICATIONS

Anonymous, "Branched esteramides, diamides or mixtures thereof and their use as solvent in phytosanitary formulations," Mar. 22, 2010; IP.com, IP.com No. IPCOM000194387D, pp. 1-37.*

Database CAPLUS [Online] Chemical Abstracts Service, Columbus, OH, US; Anon.: "Branched Esteramides, Diamides or Mixtures Thereof and Their Use as Solvent in Phytosanitary Formulations", XP002669970-& Anonymous "Branched Esteramides, Diamides or Mixtures Thereof and Their Use as Solvent in Phytosanitary Formulations"(No. IPCOM00194387D), ip.com Journal, vol. 10(4A), No. 12, Mar. 22, 2010, pp. 1-37, XP002669971.

Database CAPLUS [Online] Chemical Abstracts Service, Columbus, OH, US; Anon.: "Use of the New Esteramide Rhodiasolv Polarclean in Order to Replace Solvents With Bad HSE Profiles Such as N-Methyl Pyrrolidone (NMP), Dimethyl Formamide (DMF), Dimethyl Acetamide (DMAC), or Flammble Solvents Such as Acetone, in Various Applications", XP002669972, (2002).

* cited by examiner

COMPOSITION, METHOD FOR PRODUCING THE COMPOSITION, AND PHYTOSANITARY FORMULATION CONTAINING SAME

BACKGROUND OF THE INVENTION

The present invention relates to a composition that may in particular be used as solvent composition in phytosanitary formulations, the method for producing the composition and phytosanitary formulations containing the same.

A number of chemicals are used as solvents in industry, for example for preparing chemical products and materials, for formulating chemical compounds, or for treating surfaces. For example, solvents are used for the formulation of plant protection active substances in particular in the form of Emulsifiable Concentrates ("EC") meant to be diluted with water by the farm operator prior to being applied over a field.

Thus, the phytosanitary formulations must allow for easy dilution by weight by the farm operator in order to obtain a product in which the phytosanitary product is properly dispersed, for example in the form of a solution, emulsion, suspension, or suspo emulsion. Phytosanitary formulations thus make it possible to transport a phytosanitary product in a relatively concentrated form, and allows for easy packaging and/or easy handling for the end user. Various different types of phytosanitary formulations can be used for different phytosanitary products. These include for example Emulsifiable Concentrates ("EC"), concentrated emulsions (Emulsion in water "EW"), micro emulsions ("ME"), Wettable Powders ("WP") and granules that are dispersible in water (Water Dispersible Granules, "WDG"). Formulations that may possibly be used depend upon the physical form of the phytosanitary product (for example solid or liquid), and its physical-chemical properties in the presence of other compounds such as water or solvents.

After being diluted by weight by the farm operator, for example by mixing with water, the phytosanitary product may be present in various physical forms: solution, solid particle dispersion, dispersion of droplets of the product, droplets of solvent in which the product is dissolved, etc. Phytosanitary formulations generally comprise compounds that provide the ability to obtain these physical forms. They may be, for example, surfactants, solvents, mineral support media, and/or dispersants. Quite often these compounds do not have an active nature, but are meant rather to be of an intermediary assisting nature in the formulation. It is therefore quite often desirable to limit the quantity thereof in order to reduce the costs and/or any potential harm to the environment. Phytosanitary formulations may in particular be in liquid or solid form.

For practical reasons (for example, for reasons related to ease of handling and/or transportation), it may be preferable at times to use phytosanitary formulations in solid form, and to use formulations in liquid form at other times.

For the purpose of preparing phytosanitary formulations of solid phytosanitary active substances, it is a known technique to dissolve the product in a solvent. The phytosanitary formulation thus comprises a solution of the product in the solvent. The formulation may be in solid form, for example as a wettable powder (WP) where the adsorbed solution is an inorganic carrier material, for example kaolin and/or silica. The formulation may alternatively be in liquid form, for example in the form of an emulsifiable concentrate (EC) having a single clear liquid phase comprising the solvent and the product in solution, which is capable of forming an emulsion by addition of water, with no stirring or with very little stirring. It may also be in the form of a concentrated emulsion (EW), cloudy in appearance, of which the water dispersed phase comprises the solvent and the product in solution in the solvent. It may also be in the form of a clear micro emulsion (ME), of which the water dispersed phase comprises the solvent and the product in solution in the solvent.

Certain solid phytosanitary active substances are often difficult to formulate. For example, tebuconazole is a highly effective fungicide whose use is widespread, in particular for the cultivation of soybeans. For some phytosanitary active substances, it is difficult to produce concentrated formulations, which may be easily diluted by the farm operator, that are stable, and present no substantial disadvantages (real or perceived) in terms of safety, toxicity and/or eco toxicity. In case of some active substances, it is difficult to produce them at relatively high concentrations, with sufficient stability. In particular, it is necessary to prevent the appearance of crystals especially at low temperatures and/or during dilution thereof and/or during storage at high temperature of the diluted composition. The crystals may cause negative effects, in particular by clogging the filters of devices used to spread the diluted composition, clogging the spraying devices, reducing the overall activity of the formulation, creating unnecessary problems of waste stream channels for removing the crystals and/or resulting in poor distribution of the active ingredient in the cultivation site.

The use of solvent systems based on N-methylpyrrolidone (NMP) as a co-solvent is already known. This co-solvent provides the ability to improve the solubilisation of a large number of active substances, and to prevent the formation of crystals, however, it is found to be toxic to the reproductive system (reprotoxic) and as such as being potentially hazardous, in particular for the operators and users who handle it. There is a need for alternative solvent systems, presenting in particular:

a high degree of modularity, that is to say, an ability to be used for a large number of active substances, potential for solubilisation of significant quantities of active substances, high compatibility of several active substances in order to overcome the resistance phenomena, absence of crystallisation, even in demanding conditions, and/or a safety, toxicology and/or eco toxicology profile perceived to be favourable.

The agrochemical industry is looking for new solvent compositions having properties that are satisfactory for phytosanitary application, like for example, good solvent power for phytosanitary active substances as well as low miscibility with water. In addition, the cost of the solvent compositions should be modest, and they should have a favourable toxicology and/or eco toxicology profile, in particular low toxicity and/or low hazard potential, low volatility (low VOC—volatile organic compounds) and high degree of biodegradability.

Some compounds that are known such as Polarclean® or N-methylpyrrolidone (NMP) or Dimethyl Sulfoxide (DMSO) are good solvents for phytosanitary active substances. However, their immiscibility with water is yet to be improved, especially when the intended application is the preparation of emulsifiable concentrates.

Also known are compounds such as dimethylocta decamides or alkyl dimethylamides (ADMA), which are immiscible with water but do not have a suitable solvent power that is satisfactory for a wide range of active ingredients.

Hence the inherent problem in this domain pertains to providing a compound that has both a good solvent power as well as satisfactory water miscibility properties.

SUMMARY OF THE INVENTION

To overcome the above drawbacks, the present invention provides a novel composition that has both a good solvent power as well as satisfactory water miscibility properties.

Thus, the present invention relates to a composition comprising:

from 10% to 90% by weight of a mixture M of compounds A having the formula (I):

the said mixture comprising at least two compounds A corresponding to different formulas (I);
wherein:
$R^1$ is a linear or branched, saturated aliphatic group, having 1 to 6 carbon atoms, in which one or more hydrogen atoms are substituted by functional groups selected from among —OH groups and —COOR groups, where R is an alkyl group having 1 to 4 carbon atoms, and $R^4$ and $R^5$, which are identical or different, are methyl or ethyl groups;
$R^2$ and $R^3$, which are identical or different, are methyl or ethyl groups; $R^1$ and $R^2$ or $R^3$ may together form a ring, the said ring containing 4 to 6 carbon atoms and in which one or more hydrogen atoms may be substituted by alkyl groups having 1 to 4 carbon atoms or functional groups selected from among —OH groups, —OR groups, —COOR groups and —CONR$^4$R$^5$ groups, wherein R is an alkyl group having 1 to 4 carbon atoms, and $R^4$ and $R^5$, which are identical or different, are methyl or ethyl groups; and from 10% to 90% by weight of at least one compound B selected from amide solvents, possibly in combination with an ester solvent.

Thus, the compositions of the invention comprise a mixture of several compounds having formula (I), and in particular at least two distinct compounds.

The abscissa axis (x axis) represents the content of the solvent Rhodiasolv® Iris in the solvent Rhodiasolv® Polarclean and the vertical axis (y axis) represents the solubility of the mixture of these solvents in water (% w/w).

The dotted line curve with the black diamonds represents the points where the said mixture of solvents is not soluble in water and the solid line curve with black squares represents the points where the said mixture of solvents is soluble in water.

Figure 2:
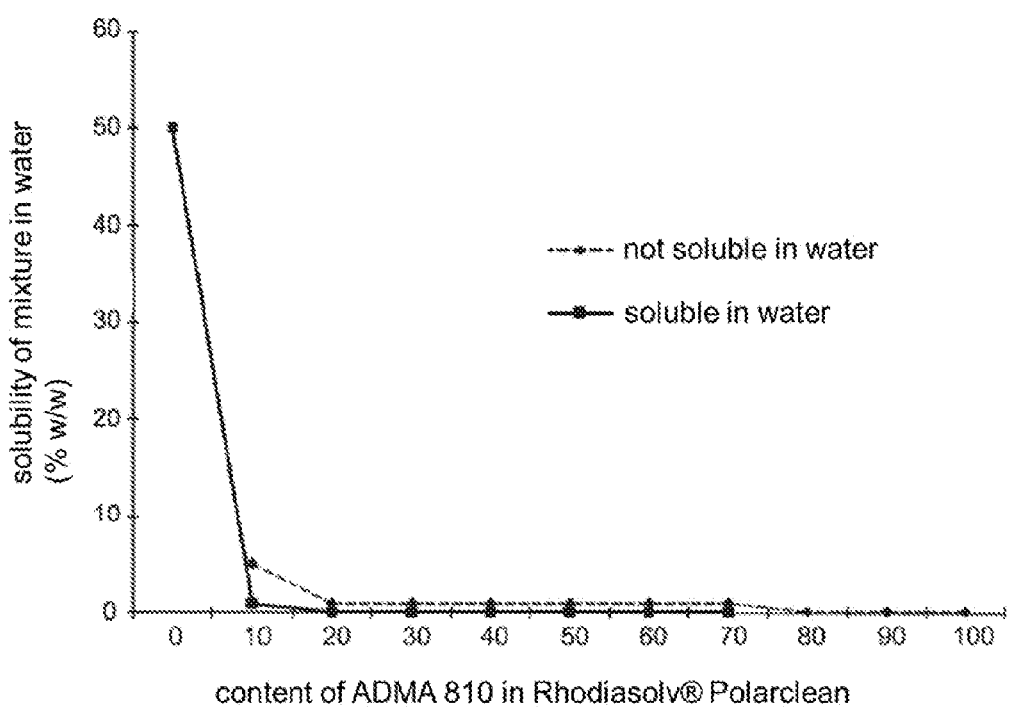

FIG. 2 shows the solubility in water of a composition according to the invention comprising a mixture of the products Rhodiasolv® Polarclean and ADMA 810 (alkyldimethylamide), with different product content levels for each of these products.

The abscissa axis (x axis) represents the content of the solvent ADMA 810 in the solvent Rhodiasolv® Polarclean and the vertical axis (y axis) represents the solubility of the mixture of these solvents in water (% w/w).

The dotted line curve with the black diamonds represents the points where the said mixture of solvents is not soluble in water and the solid line curve with black squares represents the points where the said mixture of solvents is soluble in water.

DETAILED DESCRIPTION

According to the invention, the mixture M comprises at least two different compounds, and hence corresponds to the formula (I) with different values for $R^1$, $R^2$ or $R^3$.

Preferably, the mixture M is a mixture of two different compounds each having the formula (I).

Preferably, in the formula (I), $R^1$ represents a linear or branched, saturated, acyclic aliphatic group, having 1 to 6 carbon atoms.

The hydrocarbon chain may possibly be interrupted by a heteroatom (for example, oxygen or sulfur) or a functional group (carbonyl) or carrier of one or more substituents (for example formyl) to the extent that the latter do not act as impediments with regard to the reaction conditions or the intended application.

According to the invention, at least one hydrogen atom of the $R^1$ group is substituted with an —OH group or a —COOR group, with R being as defined here above. Preferably, at least one hydrogen atom of the $R^1$ group is substituted by a —COOR group, with R being as defined here above.

With respect to $R^1$, from among the linear or branched, saturated aliphatic groups, the alkyl groups having from 1 to 6 carbon atoms in particular are envisaged.

By way of preferred examples for $R^1$, the alkyl groups having 1 to 4 carbon atoms may be mentioned.

In the formula (I), $R^1$ may also represent a monocyclic carbocyclic group. The number of carbon atoms in the ring may vary from 3 to 6 carbon atoms but it is preferably equal to 5 or 6 carbon atoms.

By way of preferred examples of monocyclic and carbocyclic groups for $R^1$, cyclopentyl or cyclohexyl groups may be cited.

According to the present invention, the "alkyl" radicals represent, branched or straight chain, saturated hydrocarbon radicals comprising from 1 to 6 carbon atoms, in particular 1 to 4 carbon atoms (they may typically be represented by the formula $C_nH_{2n+1}$, with n being an integer representing the number of carbon atoms).

When they are linear, these may include methyl, ethyl, propyl, butyl, pentyl, and hexyl radicals. When they are branched or substituted by one or more alkyl radicals, these may include isopropyl, tertbutyl, 2-ethylhexyl, 2-methylbutyl, 2-methylpentyl and 1-methylpentyl radicals.

In the context of the present invention, when $R^1$ and $R^2$ or $R^1$ and $R^3$ together form a ring, the ring also comprises the group —CON—.

According to one embodiment, the mixture M comprises at least one compound A having the formula (I), in which $R^1$ is a group having the formula —Z—COOR', where Z is a linear or branched divalent alkylene group comprising from 2 to 4 carbon atoms and R' is a methyl group.

According to one embodiment, the mixture M is a mixture of compounds having the formula (I-1) R'OOC—Z—CONR$^2$R$^3$, in which Z, R', $R^2$ and $R^3$ are as defined here above.

According to a particular embodiment, the compositions of the invention comprise at least one compound A having the following formula MeOOC—Z—CONR$^2$R$^3$, where Z, $R^2$ and $R^3$ are as defined here above.

According to one embodiment, the mixture M is a mixture of compounds having the formula (I-2) MeOOC—Z—CONR$^2$R$^3$, in which Z, R', $R^2$ and $R^3$ are as defined here above.

Preferably, the compositions of the invention comprise at least one compound A having the following formula MeOOC—Z—CONR²R³, where R² and R³ are as defined here above and Z is a branched alkyl group having 2 to 4 carbon atoms.

According to one embodiment, the mixture M is a mixture of compounds having the formula (I-3) MeOOC—Z—CONR²R³, in which R', R² and R³ are as defined here above, and Z is a branched alkyl group having 2 to 4 carbon atoms.

According to one embodiment, the mixture M is a mixture of compounds having the formula (I) comprising:

a compound having the formula (I) wherein R¹ is —CH(CH₂—CH₃)—CH₂—COOMe, a compound having the formula (I) wherein R¹ is —CH₂—CH(CH₂—CH₃)—COOMe a compound having the formula (I) wherein R¹ is —CH(CH₃)—CH₂—CH₂—COOMe, and a compound having the formula (I) wherein R¹ is —CH₂—CH₂—CH(CH₃)—COOMe.

According to one embodiment, the mixture M of compounds having the formula (I) as defined here above further comprises a compound having the formula (I) wherein R¹ is —(CH₂)₄—COOMe.

Thus, the compositions of the invention may comprise a compound A having the following formula MeOOC—(CH₂)₄—CONR²R³, where R² and R³ are as defined here above.

According to one embodiment, the mixture M comprises at least one compound A having the formula (I) wherein R¹ is a 1-hydroxyethyl group.

According to one embodiment, the mixture M comprises at least one compound A having the formula (I) wherein R² and R³ are methyl groups.

A particular family of compounds A according to the invention therefore corresponds to the formula R¹CONMe₂.

According to another embodiment, the composition of the invention comprises at least one compound A having the formula (I), wherein R¹ and R² together form a ring, the said ring having 4 carbon atoms, the carbon of the carbonyl being included, and R³ is a methyl group.

According to the invention, the compound B is an amide solvent or a mixture of several amide solvents.

According to one embodiment, the compound B is an amide solvent.

Thus, according to one embodiment, the compositions of the invention comprise, or are constituted of, an amide solvent and a mixture M of compounds having the formula (I-1) as defined here above.

According to one embodiment, the compositions according to the invention comprise, or are constituted of, an amide solvent and a mixture M of compounds having the formula (I-2) as defined here above.

According to one embodiment, the compositions according to the invention comprise, or are constituted of, an amide solvent and a mixture M of compounds having the formula (I-3) as defined here above.

With regard to compound B, mention may be made, for example of a mixture comprising at least one amide solvent and at least one ester solvent.

According to one embodiment, the compound B is a mixture consisting of an amide solvent and an ester solvent.

Thus, according to one embodiment, the compositions according to the invention comprise an amide solvent, an ester solvent and a mixture M of compounds having the formula (I-1) as defined here above.

Thus, according to one embodiment, the compositions according to the invention comprise an amide solvent, an ester solvent and a mixture M of compounds having the formula (I-2) as defined here above.

Thus, according to one embodiment, the compositions according to the invention comprise an amide solvent, an ester solvent and a mixture M of compounds having the formula (I-3) as defined here above.

According to one embodiment, the amide solvents correspond to the following formula (II):

$$R''—CONMe_2 \quad (II)$$

where R" is a linear or branched alkyl group, comprising of 8 to 20 carbon atoms.

Among the amide solvents, mention may be made of the compounds having the formula (II) wherein R" is selected from among the C8, C10, C12, C18 linear alkyls and mixtures thereof, in all ratios.

According to one embodiment, the compound B may also comprise in addition an aromatic solvent or a mixture of such solvents.

Among the aromatic solvents, mention may be made of toluene, xylene and mixtures of C8-C12 di- and trialkylbenzenes like Solvesso®.

Among the aromatic hydrocarbons, mention may be made of alkylbenzenes such as toluene, dialkylbenzenes such as xylene, polynuclear aromatic hydrocarbons such as naphthalenes, alkyl naphthalenes (for example dimethylnaphthalene), dialkylnaphthalenes, trialkylnaphtalenes such as dimethylmonoisopropylnaphtalene and phenylxylylethane, as well as mixtures thereof.

The majority of these hydrocarbons are obtained by fractionation of crude oil and in general, have distillation ranges comprised from about 135° C. to about 305° C., those with temperatures of about 183° C. to about 290° C. being preferred.

Among the aromatic hydrocarbons, the following commercial products may also be mentioned: Nisseki Hisol SAS-296 (a mixture of 1-phenyl-1-xylylethane and 1-phenyl-1-ethylphenylethane, Nippon Oil Corporation), Cactus Solvent HP-MN (methylnaphthalene 80%, Japan Energy Corporation), Cactus Solvent HP-DMN (dimethylnaphthalene 80%, Japan Energy Corporation), Cactus Solvent P-100 (alkylbenzene with 9 to 10 carbon atoms, Japan Energy Corporation), Cactus Solvent P-150 (alkylbenzene, Japan Energy Corporation), Cactus Solvent P-180 (a mixture of methylnaphthalene and dimethylnaphthalene, Japan Energy Corporation), Cactus Solvent P-200 (a mixture of methylnaphthalene and dimethylnaphthalene, Japan Energy Corporation), Cactus Solvent P-220 (a mixture of methylnaphthalene and dimethylnaphthalene, Japan Energy Corporation), Cactus Solvent PAD-1 (dimethylmonoisopropylnaphtalene, Japan Energy Corporation), Solvesso 100 (aromatic hydrocarbon, Exxon Mobil Corporation), Solvesso 150 (aromatic hydrocarbon, Exxon Mobil Corporation), Solvesso 200 (aromatic hydrocarbon, Exxon Mobil Corporation), ULTRA LOW NAPHTHALENE AROMATIC 150 (ExxonMobil Chemical Company), ULTRA LOW NAPHTHALENE AROMATIC 200 (ExxonMobil Chemical Company), Solvesso 150 ND (aromatic hydrocarbon, Exxon Mobil Corporation), Solvesso 200 ND (aromatic hydrocarbon, Exxon Mobil Corporation) Swasol 100 (toluene, Maruzen Petrochemical Co Ltd) and Swasol 200 (xylene, Maruzen Petrochemical Co Ltd).

Mention may be made in particular of the mixtures of C8-C12 di- and trialkylbenzenes with a flash point of at least 60.5° C.

Such mixtures are commercially available, in particular from Exxon Mobil under the names Solvesso 150 ® and Solvesso 200®.

According to one embodiment, the compound B may further comprise an ester solvent or a mixture of such solvents.

Among the ester solvents, mention may be made of 2-ethylhexyl lactate, alkyl acetates, esters of fatty acids, fatty esters of carboxylic acids and mixtures of methyl diesters of 2-ethyl succinic acid, methylglutaric acid and possibly adipic acid, such as Rhodiasolv® IRIS.

According to one embodiment, the compositions according to the invention comprise a fatty acid ester, for example a canola oil ester, and in particular a canola oil methyl ester.

According to one embodiment, the ester solvents of the compositions according to the invention are carboxylic acid esters, preferably mixtures of several carboxylic acid esters.

Preferably, the ester solvents of the compositions according to the invention correspond to the formula $R_aOOC-A-COOR_a$, where $R_a$ represents a linear or branched alkyl group comprising of 1 to 6 carbon atoms, and preferably represents a methyl group, and A represents a linear or branched alkylene group comprising of 2 to 4 carbon atoms.

According to one embodiment, the ester solvent is the compound Rhodiasolv® IRIS which is a mixture comprising of 70% to 95% by weight of dimethyl 2-methyl glutarate, 5% to 30% by weight of dimethyl ethylsuccinate and 0% to 10% by weight of dimethyl adipate.

The compound B may be a mixture of solvents. Thus, the compound B may be either a mixture of amide solvents, or a mixture of an amide solvent and an ester solvent, or a mixture of amide solvents with an ester solvent, or a mixture of amide solvents and ester solvents, or even one of the above mixtures comprising in addition at least one aromatic solvent.

The present invention also relates to a composition as defined here above, comprising:
  from 20% to 60% by weight of the mixture M as defined here above, and
  from 40% to 80% by weight of the compound B as defined here above.

According to a particular embodiment, the present invention relates to a composition as defined here above, comprising:
  from 20% to 60% by weight of a mixture M of compounds having the formula (I) comprising:
    a compound having the formula (I) where $R^1$ is —CH(CH$_2$—CH$_3$)—CH$_2$—COOMe,
    a compound having the formula (I) where $R^1$ is —CH$_2$—CH(CH$_2$—CH$_3$)—COOMe,
    a compound having the formula (I) where $R^1$ is —CH(CH$_3$)—CH$_2$—CH$_2$—COOMe,
    a compound having the formula (I) where $R^1$ is —CH$_2$—CH$_2$—CH(CH$_3$)—COOMe, and
    as appropriate a compound having the formula (I) where $R^1$ is —(CH$_2$)$_4$—COOMe;
  from 40% to 80% by weight of the compound B as defined here above.

According to one embodiment, the compositions according to the invention consist of a mixture of ester amide compounds having the formula (I), in particular corresponding to the mixture as defined here above, of an amide solvent, preferably having the formula R"—CONMe$_2$, where R" represents a linear C10 alkyl chain, and an ester solvent, preferably selected from the esters, in particular methyl esters, of carboxylic acids or the esters, in particular methyl esters, of fatty acids.

According to a particular embodiment, the present invention relates to a composition as defined here above, comprising:
  from 20% to 60% by weight of a mixture M of compounds having the formula (I) comprising:
    a compound having the formula (I) where $R^1$ is —CH(CH$_2$—CH$_3$)—CH$_2$—COOMe,
    a compound having the formula (I) where $R^1$ is —CH$_2$—CH(CH$_2$—CH$_3$)—COOMe,
    a compound having the formula (I) where $R^1$ is —CH(CH$_3$)—CH$_2$—CH$_2$—COOMe,
    a compound having the formula (I) where $R^1$ is —CH$_2$—CH$_2$—CH(CH$_3$)—COOMe, and
    as appropriate a compound having the formula (I) where $R^1$ is —(CH$_2$)$_4$—COOMe;
  from 30% to 70% by weight of an amide solvent as defined here above; and
  from 0% to 25% by weight of an ester solvent as defined here above.

According to a particular embodiment, the present invention relates to a composition as defined here above, comprising:
  from 40% to 60% by weight of a mixture M of compounds having the formula (I) comprising:
    a compound having the formula (I) where $R^1$ is —CH(CH$_2$—CH$_3$)—CH$_2$—COOMe,
    a compound having the formula (I) where $R^1$ is —CH$_2$—CH(CH$_2$—CH$_3$)—COOMe,
    a compound having the formula (I) where $R^1$ is —CH(CH$_3$)—CH$_2$—CH$_2$—COOMe,
    a compound having the formula (I) where $R^1$ is —CH$_2$—CH$_2$—CH(CH$_3$)—COOMe, and
    as appropriate a compound having the formula (I) where $R^1$ is —(CH$_2$)$_4$—COOMe; and
  from 40% to 60% by weight of an amide solvent as defined here above.

According to a particular embodiment, the present invention relates to a composition as defined here above, comprising:
  from 30% to 55% by weight of a mixture M of compounds having the formula (I) comprising:
    a compound having the formula (I) where $R^1$ is —CH(CH$_2$—CH$_3$)—CH$_2$—COOMe,
    a compound having the formula (I) where $R^1$ is —CH$_2$—CH(CH$_2$—CH$_3$)—COOMe,
    a compound having the formula (I) where $R^1$ is —CH(CH$_3$)—CH$_2$—CH$_2$—COOMe,
    a compound having the formula (I) where $R^1$ is —CH$_2$—CH$_2$—CH(CH$_3$)—COOMe, and
    as appropriate a compound having the formula (I) where $R^1$ is —(CH$_2$)$_4$—COOMe;
  from 30% to 55% by weight of an amide solvent as defined here above; and
  from 10% to 25% by weight of an ester solvent as defined here above.

The present invention also relates to a method for obtaining a composition of solvents having a water solubility of less than or equal to 1% by weight at 20° C.-25° C., characterised in that it involves mixing from 10% to 90% by weight of at least one mixture M as defined here above, with 10% to 90% by weight of at least one compound B as defined here above.

The present invention also relates to the use of the composition as defined here above as a solvent having a water solubility of less than or equal to 1% by weight at 20° C.-25° C.

The present invention also relates to a phytosanitary formulation comprising of at least one phytosanitary active ingredient and, by way of a solvent for at least one phytosanitary active substance, the composition as defined here above.

The phytosanitary formulation is generally a concentrated phytosanitary formulation containing a phytosanitary active compound.

The agricultural sector uses numerous active materials such as fertilizers or pesticides, for example insecticides, herbicides or fungicides. The reference is to active phytosanitary products (or active materials). Active phytosanitary products are generally produced in pure or highly concentrated form. They are to be used on agricultural operation sites in low concentrations. To this end, they are usually formulated with other ingredients in order to enable easy dilution by weight by the farm operator. The reference is to phytosanitary formulations. The dilution carried out by the farm operator is generally performed by mixing the phytosanitary formulation with water.

According to a particular embodiment, the phytosanitary formulation of the invention is in the form of an emulsifiable concentrate, a concentrated emulsion or a micro emulsion.

The formulations comprising the solvent of the invention, that is, the composition comprising at least one mixture M and at least one compound B, present in particular:
- potential for solubilisation of significant quantities of active substances,
- absence of crystallisation, even in demanding conditions,
- a good level of biological activity that may be due to good solvation, and/or
- a safety, toxicology and/or eco toxicology profile perceived to be favourable.

The phytosanitary formulation may in addition also be a concentrated phytosanitary formulation comprising:
a) an active phytosanitary product,
b) the solvent (composition according to the present invention)
c) possibly at least emulsifying agent, preferably a surfactant, and
d) possibly water.

Active phytosanitary products, in particular products that are not soluble in water and solids are known to the person skilled in the art. The active phytosanitary product may in particular be a herbicide, an insecticide, a miticide, a fungicide, or an agent for exterminating rodents ("rodenticide" in English), for example a rat poison.

By way of examples of insecticides and miticides suitable for the invention, mention could be made of those belonging to the following families:
organo halogenated or chlorinated compounds, such as for example DDT (dichloro diphenyl trichloroethane), lindane (γ isomer of hexachloro cyclohexane), chlordane (octachlorotetrahydro methano indene), toxaphene;
carbinols such as dicofol (dichlorophenyl trichloroethanol) for example;
organophosphates, such as for example bromophos [(4-bromo-2,5-dichloro-phenoxy)-dimethoxy-thioxo-phosphorane), diazinon (O,O-diethyl-O-(2-isopropyl-6-methyl-pyrimidin-4-yl)phosphorothioate), fenitrothion (O,O-Dimethyl O-4-nitro-m-tolyl phosphorothioate), malathion (S-1,2-bis(ethoxycarbonyl) ethyl O,O-dimethyl phosphorodithioate), parathion (O,O-diethyl-O-4-nitrophenyl phosphorothioate), trichlorfon (dimethyl 2,2,2-trichloro-1-hydroxy-ethylphosphonate], dimethoate (O,O-dimethyl S-methyl-carbamoylmethyl phosphorodithioate);
sulfones and sulfonates such as for example tetradifon (tetrachloro diphenyl sulfone);
carbamates, such as for example carbaryl (naphthyl N-methylcarbamate), methomyl ((methylthio ethylidene amine)N-methylcarbamate);
benzoylureas such as for example diflubenzuron (difluoro benzoyl chlorophenylurea);
the synthetic pyrethroids;
acaricides such as for example cyhexatin (tricyclohexyl hydroxystannane).

Fungicides that may be put to use in the invention may for example be selected from among:
carbamates such as benomyl (methyl butylcarbamoyl benzimidazolyl carbamate), carbendazim (methyl benzimidazol carbamate), ziram (zinc dimethyl dithiocarbamate), zineb (zinc ethylene-bis dithiocarbamate), maneb (manganese ethylene-bis dithiocarbamate), mancozeb (manganese and zinc ethylene bis-dithiocarbamate), thiram (bis dimethyl-thiocarbamoyl disulfide);
benzene derivatives such as for example PCNB (pentachloronitrobenzene);
phenol derivatives such as for example dinocap ((methyl-heptyl)dinitrophenyl crotonate);
quinones such as for example dithianon (dioxodihydro naphtho dithiin dicarbonitrile);
dicarboximides, such as, for example, captan (trichloromethylthio tetrahydroisoindolinedione), folpel (trichloromethylthio isoindolinedione), and iprodione (dichlorophenyl isopropyl carbamoyl dichlorophenylhydantoine);
amines and amides, such as, for example, benodanil (iodobenzanilide), and metalaxyl (methyl dimethylphenyl methoxyacetyl alalinate);
diazines, such as, for example, pyrazophos (ethyl and ethoxycarbonyl methyl pyrazolo pyrimidine thiophosphate), fenarimol (chlorophenyl chlorophenyl pyrimidine methanol);
sulfamides and sulfur containing derivatives such as for example dichlofluanide (dichloro fluoro methylthiodimethyl phenyl sulfamide);
guanidines such as for example doguadine (dodecylguanidine acetate);
heterocycles such as for example etridiazole (ethoxy trichloromethyl thiadiazole), triadimefon (chlorophenoxy dimethyltriazole butanone);
metal monoethyl phosphites such as for example phosethyl-Al (aluminium tris-O-ethylphosphonate);
organostannic compounds such as for example fentin-acetate (triphenyl tin).

By way of chemical substances having herbicidal properties, it is possible to resort to those which are found in the following chemical formulae:
Phenolic compounds such as, for example, dinoseb (dinitrobutylphenol);
carbamates such as, for example phenmedipham (methyl tolylcarbamoyloxyphenyl carbamate);
substituted ureas such as for example neburon (butyl dichlorophenyl methyl urea), diuron (dichlorophenyl dimethyl urea), linuron (dichlorophenyl methoxymethyl urea);
diazines such as for example, bromacil (bromobutyl methyl uracil), chloridazone (phenylamino chloropyridazone);
triazines such as for example, simazine (chloro bis-ethylamino s-triazine), atrazine (chloroethylamino isopropylamino-s-triazine), terbutylazine (chloroethylamino butylamino s-triazine), terbumeton (tert-butylamino ethylamino methoxy triazine), prometryne (methylthio bis isopropylamino s-triazine), ametryne (methylthio ethylamino isopropylamino s-triazine), metribuzin (methylthio butylamino triazine-one), cyanazine (chloro ethylamino s-triazine-ylaminomethyl-propionitrile);
amides such as for example napropamide (naphthoxydiethyl propionamide), propachlor (isopropyl chloroacetanilide);
quaternary ammoniums;
benzonitriles;

toluidines such as for example ethalfluraline (dinitro-ethylmethyl propenyl trifluoro methylaniline), oryzalin (dinitrodipropyl sulfanil-amide);

triazoles;

various derivatives such as for example benazolin (chloro oxo benzothiazoline acetic acid), dimefuron (chloro oxo tert-butyl oxadiazoline phenyl dimethyl urea), bromophenoxime (dibromo hydroxy dinitro phenyl benzaldoxime), pyridate (octyl chlorophenylpyridazinylcarbothiolate).

By way of other examples of biocides that may be used according to the invention, mention may be made of nematicides, molluscicides etc. It is possible to apply one or more active materials belonging to the same class of biocides or to a different class thereof.

Thus, by way of non-limiting examples of preferred active materials, mention may be made inter alia of Ametryne, Diuron, Linuron, Chlortoluron, Isoproturon, Nicosulfuron, Metamitron, Diazinon, Aclonifen, Atrazine, Chlorothalonil, Bromoxynil, Bromoxynil heptanoate, Bromoxynil octanoate, Mancozeb, Maneb, Zineb, Phenmedipham, Propanyl, the phenoxyphenoxy series, the series of heteroaryloxyphenoxy, CMPP, MCPA, 2,4-D, Simazine, active products from the series of imidazolinones, the organophosphorus family, with notably Azinphos-ethyl, Azinphos-methyl, Alachlor, Chlorpyriphos, Diclofop-methyl, Fenoxaprop-p-ethyl, Methoxychlor, Cypermethrin, Fenoxycarb, cymoxanil, chlorothalonyl, neonicotinoid insecticides, the family of triazole fungicides such as azaconazole, bromuconazole, cyproconazole, difenoconazole, diniconazole, epoxyconazole, fenbuconazole, flusilazole, myclobutanyl, tebuconazole, triadimefon, triadimenol, strobilurins such as pyraclostrobin, picoxystrobin, azoxystrobine, famoxadone, kresoxym-methyl and trifloxystrobine, sulfonylureas such as bensulfuron-methyl, chlorimuron-ethyl, chlorsulfuron, metsulfuron-methyl, nicosulfuron, sulfomethuron-methyl, triasulfuron, tribenuron-methyl.

Non water-soluble products are selected from this list.

The following active phytosanitary products may in particular be put to use:

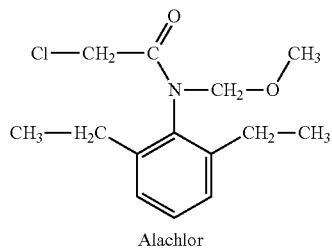
Alachlor

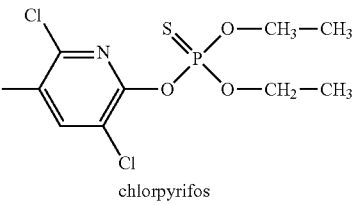
chlorpyrifos

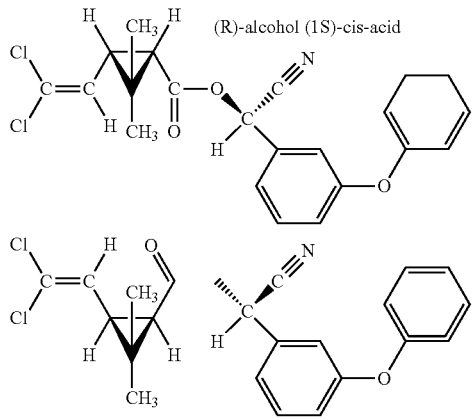
(R)-alcohol (1S)-cis-acid (S)-alcohol (1R)-cis-acid

As a racemic mixture and/or as isolated stereoisomers.

Alpha cypermethrin

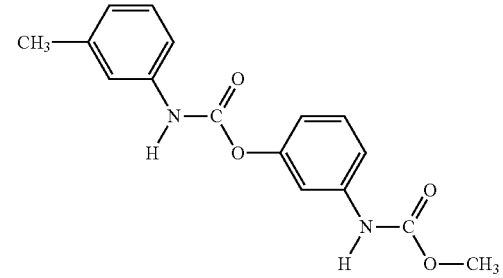
Phenmedipham

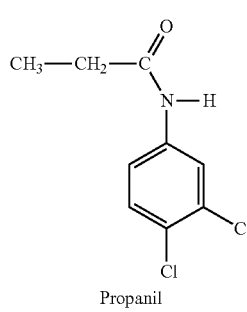
Propanil

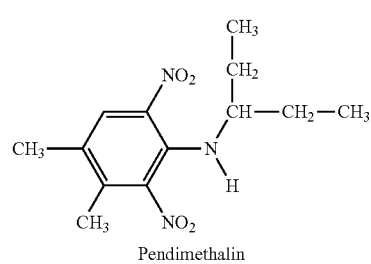
Pendimethalin

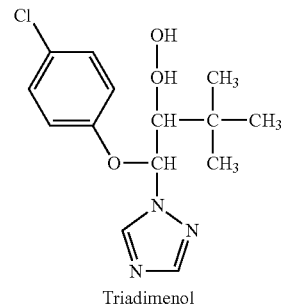
Triadimenol

-continued
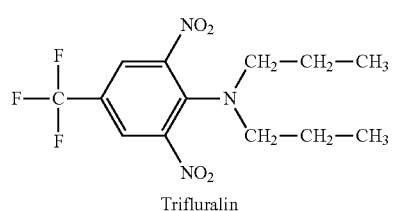
Trifluralin
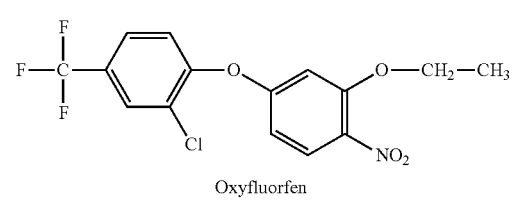
Oxyfluorfen
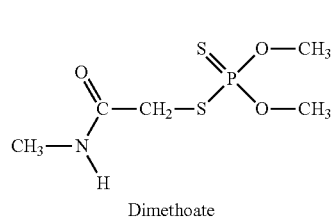
Dimethoate
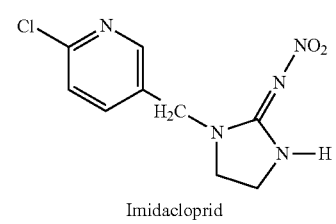
Imidacloprid
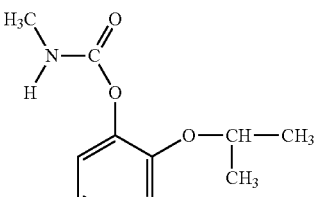
Propoxur
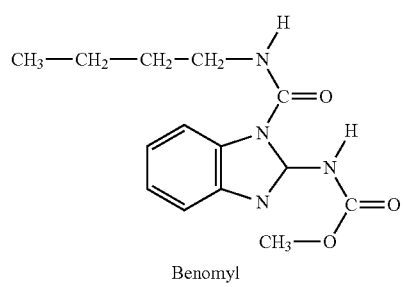
Benomyl
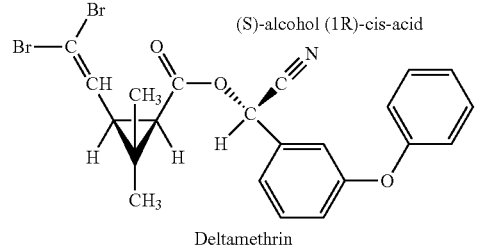
Deltamethrin
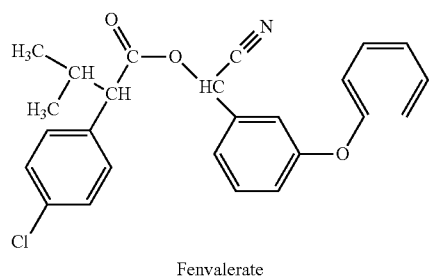
Fenvalerate
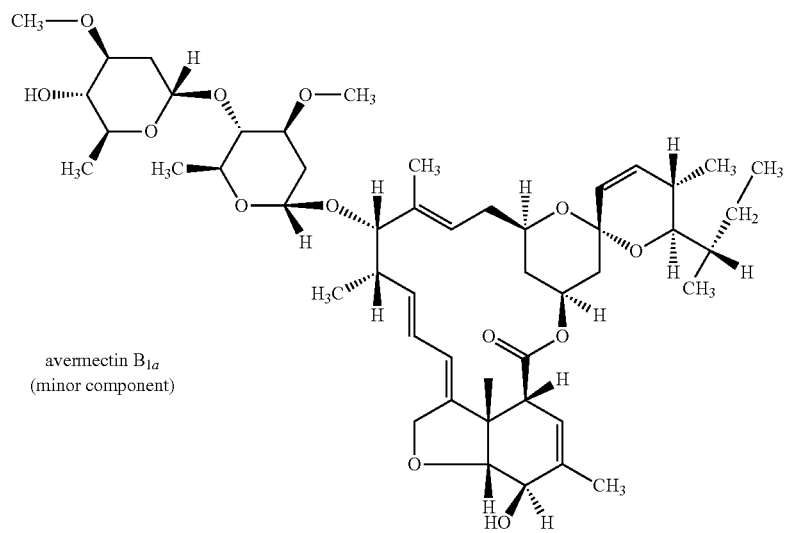
avermectin $B_{1a}$
(minor component)

-continued
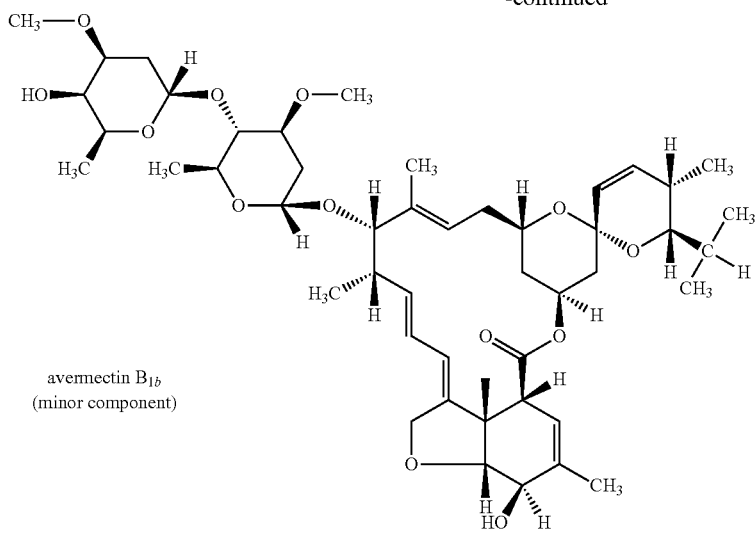
avermectin B$_{1b}$
(minor component)
Abamectin
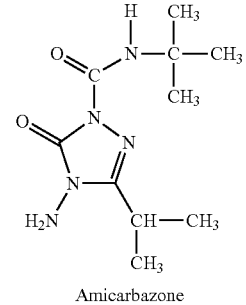
Amicarbazone
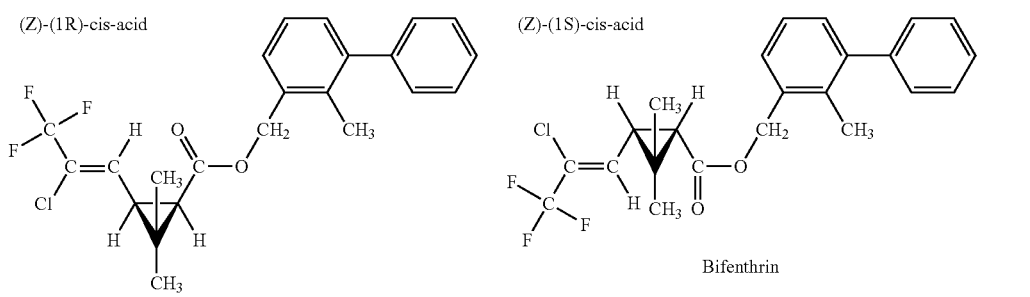
(Z)-(1R)-cis-acid    (Z)-(1S)-cis-acid
Bifenthrin
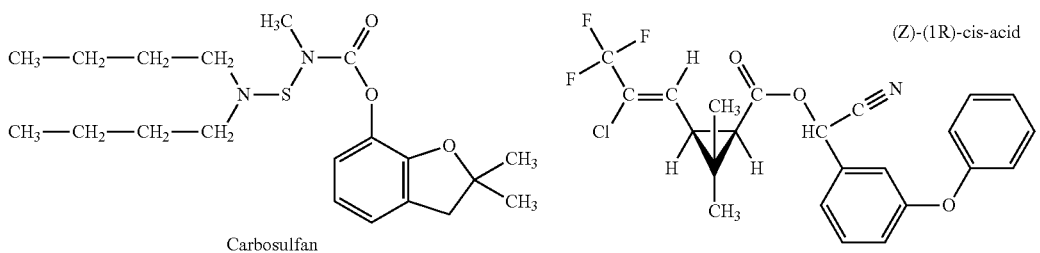
Carbosulfan    (Z)-(1R)-cis-acid
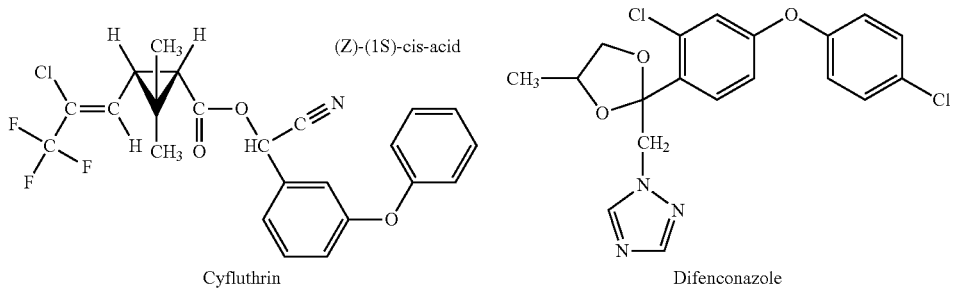
(Z)-(1S)-cis-acid
Cyfluthrin    Difenconazole
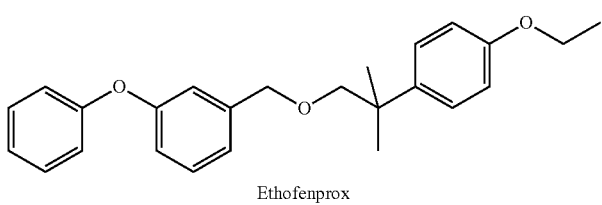
Ethofenprox -continued
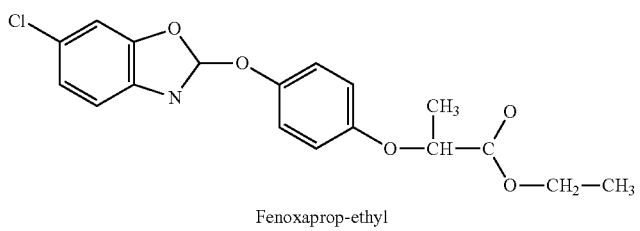
Fenoxaprop-ethyl
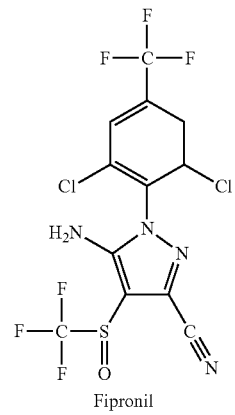
Fipronil
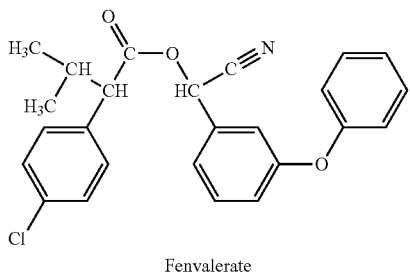
Fenvalerate
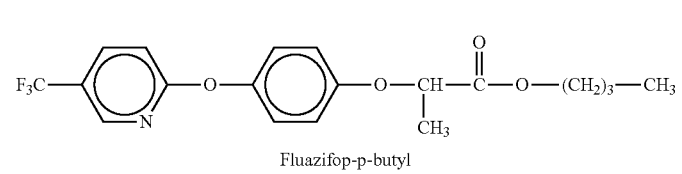
Fluazifop-p-butyl
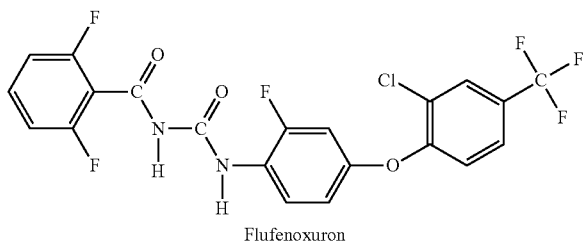
Flufenoxuron
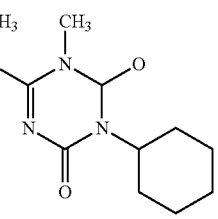
Hexazinone
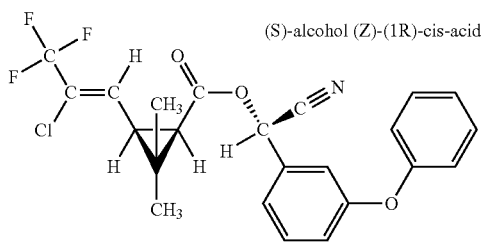
(S)-alcohol (Z)-(1R)-cis-acid
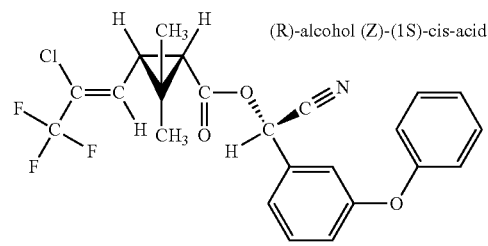
(R)-alcohol (Z)-(1S)-cis-acid
Lambda-cyalothrin
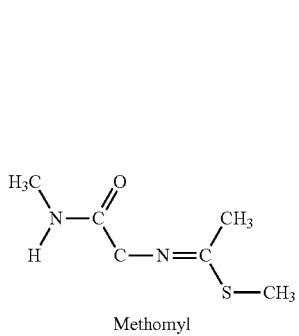
Methomyl
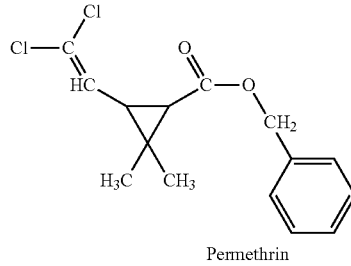
Permethrin
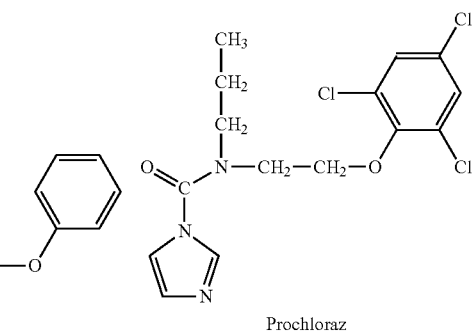
Prochloraz -continued

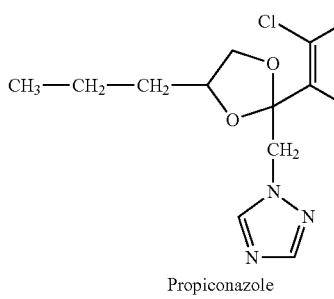
Propiconazole

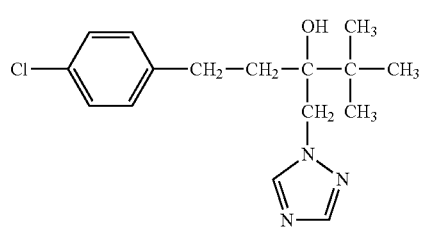
Tebuconazole

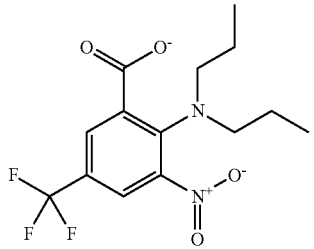
Trifluralin

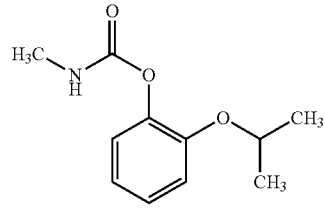
Propoxur

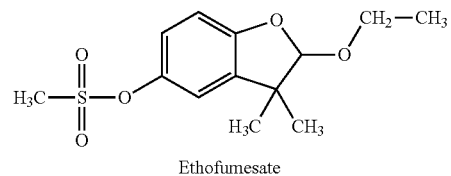
Ethofumesate

According to one embodiment, the phytosanitary active ingredient is selected from among the following compounds:
Abamectin,
Alachlor
Bromoxynil
Chlorpyrifos,
Alpha-cypermethrin,
Cyfluthrin,
Ethofenprox,
Flufenoxuron,
Lufenuron,
Myclobutanil,
Phenmedipham,
Prochloraz,
Propanil,
Pendimethalin,
The azoles, preferably triazoles, preferably tebuconazole or uniconazole,
Triadimenol,
Trifluralin,
Oxyfluorfen,
Imidacloprid,
Ethofumesate,
Dimethyl phosphate (DMP)
Dimethoate,
Propoxur, and mixtures thereof.

These products and names are known to the person skilled in the art. It is possible to combine several active phytosanitary products.

The present invention also relates to a phytosanitary formulation as defined here above, in which the composition as defined here above is representative of 10% to 90% by weight relative to the weight of the formulation.

The phytosanitary formulation may also comprise a surfactant, preferably an emulsifier. Emulsifiers are agents that are intended to facilitate emulsification after the formulation is placed in the presence of water, and/or stabilisation (over time and/or in temperature) of the emulsion, for example by avoiding separation of the phases.

The surfactant may be an anionic, non-ionic, preferably polyalkoyxlated, cationic, amphoteric (a term also including zwitterionic surfactants) surfactant. This may be a mixture or a combination of these surfactants.

By way of examples of anionic surfactants, mention may be made without any intended limitation thereto, of:
alkylsulfonic acids, arylsulfonic acids, optionally substituted with one or more hydrocarbon groups, and the acid function of which is partly or totally salified, like $C_8$-$C_{50}$ alkylsulfonic acids, more particularly $C_8$-$C_{30}$, preferably $C_{10}$-$C_{22}$ alkylsulfonic acids, benzenesulfonic acids, naphthalenesulfonic acids, substituted with one to three $C_1$-$C_{30}$, preferably $C_4$-$C_{16}$ alkyl and/or $C_2$-$C_{30}$, preferably $C_4$-$C_{16}$ alkenyl groups, mono- or di-esters of alkylsulfosuccinic acids, of which the linear or branched alkyl portion is optionally substituted with one or more linear or branched $C_2$-$C_4$ hydroxylated and/or alkoxylated (preferably ethoxylated, propyxylated, ethopropoxylated) groups, phosphate esters more particularly selected from among those comprising at least one linear or branched, saturated, unsaturated or aromatic hydrocarbon group, comprising 8 to 40 carbon atoms, preferably 10 to 30, optionally substituted with at least one alkoxylated (ethoxylated, propoxylated, ethopropoxylated) group. In addition, they comprise at least one phosphate ester group, mono- or di-esterified such that it is possible to have one or two free or partly or totally salified groups. The preferred phosphate esters are of the type of the mono- and di-esters of phosphoric acid and of alkoxylated (ethoxylated and/or propoxylated) mono-, di- or tri-styrylphenol, or alkoxylated (ethoxylated and/or propoxylated) mono-, di- or trialkyiphenol, optionally substituted with one to four alkyl groups; of phosphoric acid and of an alkoxylated (ethoxylated or ethopropoxylated) $C_8$-$C_{30}$, preferably $C_{10}$-$C_{22}$ alcohol; of phosphoric acid and of a non-alkoxylated $C_8$-$C_{22}$, preferably $C_{10}$-$C_{22}$ alcohol, sulfate esters obtained from saturated or aromatic alcohols optionally substituted with one or more alkoxylated (ethoxylated, propoxylated, ethopropoxylated) groups, and for which the sulfate functions appear in the free acid form, or are partly or totally neutralised. As an example, mention may be made of sulfate esters more particularly obtained from saturated or unsaturated $C_8$-$C_{20}$ alcohols, which may comprise 1 to 8 alkoxylated (ethoxylated, propoxylated, ethopropoxylated) units; sulfate esters obtained from polyalkoxylated phenol, substituted with 1 to 3 saturated or unsaturated $C_2$-$C_{30}$ hydroxycarbon groups, and in which the number of alkoxylated units is comprised between 2 and 40; the sulfate esters obtained from polyalkoxylated mono-, di- or tri-styrylphenol in which the number of alkoxylated units varies from 2 to 40.

The anionic surfactants may be in the acid form (they are potentially anionic), or in a partly or totally salified form with one counter-ion. The counter-ion may be an alkali metal, such as sodium or potassium, an alkaline earth metal, such as calcium, or moreover even an ammonium ion of formula $N(R)_4^+$ in which the R groups, either identical or different, represent a hydrogen atom or a $C_1$-$C_4$ alkyl group optionally substituted with an oxygen atom.

By way of examples of non-ionic surfactants, mention may be made without any intended limitation thereto, of:

polyalkoxylated (ethoxylated, propoxylated, ethopropoxylated) phenols substituted with at least one $C_4$-$C_{20}$, preferably $C_4$-$C_{12}$ alkyl group, or substituted with at least one alkylaryl group, the alkyl portion of which is a $C_1$-$C_6$ alkyl. More particularly, the total number of alkoxylated units is comprised between 2 and 100. As an example, mention may be made of polyalkoxylated mono-, di- or tri-(phenylethyl) phenols, or polyalkoxylated nonylphenols. Amongst the ethoxylated and/or propoxylated, sulfated and/or phosphated di- or tri-styrylphenols, mention may be made of ethoxylated di-(phenyl-1-ethyl)phenol, containing 10 oxyethylene units; ethoxylated di-(phenyl-1-ethyl)phenol, containing 7 oxyethylene units; sulfated ethoxylated di-(phenyl-1-ethyl)phenol, containing 7 oxyethylene units; ethoxylated tri-(phenyl-1-ethyl)phenol, containing 8 oxyethylene units; ethoxylated tri-(phenyl-1-ethyl)phenol, containing 16 oxyethylene units; sulfated ethoxylated tri-(phenyl-1-ethyl)phenol, containing 16 oxyethylene units; ethoxylated tri-(phenyl-1-ethyl)phenol, containing 20 oxyethylene units; phosphated ethoxylated tri-(phenyl-1-ethyl) phenol, containing 16 oxyethylene units.

polyalkoxylated (ethoxylated, propyxylated, ethopropoxylated) $C_6$-$C_{22}$ fatty acids or alcohols. The number of alkoxylated units is comprised between 1 and 60. The term ethoxylated fatty acid includes both the products obtained by ethoxylation of a fatty acid by ethylene oxide as well as those obtained by esterification of a fatty acid by a polyethylene glycol.

polyalkoxylated (ethoxylated, propoxylated, ethopropoxylated) triglycerides of vegetable or animal origin. Thus, may be included triglycerides from lard, tallow, ground nut oil, butter oil, cotton seed oil, flax oil, olive oil, palm oil, grapeseed oil, fish oil, soya bean oil, castor oil, rapeseed oil, coprah oil, coconut oil, and comprising a total number of alkoxylated units comprised between 1 and 60. The term ethoxylated triglyceride makes reference both to products obtained by ethoxylation of a triglyceride with ethylene oxide as well as to those obtained by transesterification of a triglyceride with a polyethylene glycol.

sorbitan esters, optionally polyalkoxylated (ethoxylated, propoxylated, ethopropoxylated), more particularly the cyclised sorbitol esters of $C_{10}$-$C_{20}$ fatty acids such as lauric acid, stearic acid, or oleic acid, and comprising a total number of alkoxylated units comprised between 2 and 50.

Useful emulsifiers are in particular the following products, all marketed by Rhodia:

Soprophor® TSP/724: a surfactant based on ethopropoxylated tristyrylphenol,

Soprophor® 796/P: a surfactant based on ethopropoxylated tristyrylphenol

Soprophor® CY 8: a surfactant based on ethoxylated tristyrylphenol

Soprophor® BSU: a surfactant based on ethoxylated tristyrylphenol

Alkamuls® RC: a surfactant based on ethoxylated castor oil

Alkamuls® OR/36: a surfactant based on ethoxylated castor oil

Alkamuls® T/20: a surfactant based on ethoxylated sorbitan ester.

Geronol® TBE724: a surfactant based on ethopropoxylated tristyrylphenol

Geronol® TEB25: a mixture of surfactants based on ethoxylated castor oil, calcium dodecyl benzene sulfonate and alkoxylated polymers.

The concentrated phytosanitary formulation preferably does not contain large amounts of water. Typically the water content is generally less than 10% by weight.

The formulation is preferably a liquid formulation, for example in the form of an emulsifiable concentrate (EC), a concentrated emulsion (EW), a soluble concentrate (SL), a suspo emulsion (SE) or a micro emulsion (ME). In that case it preferably contains less than 500 g/L of water, more preferably less than 250 g/L. It will generally be less than 100 g/L.

The formulations may advantageously comprise:

a) from 0.01% to 90% preferably 10% to 60%, of the phytosanitary product, by weight of the active material, b) from 10% to 92%, preferably 20% to 80%, of the composition according to the present invention, by weight, c) from 1% to 88%, preferably from 2% to 78% by weight, of at least one co-solvent or one other solvent, d) from 2% to 60%, preferably 5% to 50%, preferably 8% to 25%, by weight of dry matter, of a surfactant, e) from 0% to 50%, preferably 0% to 20% by weight of water.

The scope of the invention does not exclude the production of solid formulations, such as formulations in which a liquid comprising the phytosanitary product solubilised in the solvent (composition of the invention), is supported by a mineral and/or dispersed in a solid matrix.

The formulation may quite obviously include certain ingredients (or "other additives") other than the active phytosanitary product, the composition of the invention other solvent(s), the optional emulsifying agent(s) and the optional water. It may include, in particular viscosity modifying agents, antifoam agents and defoamers, in particular silicone antifoams and defoamers, anti-rebound agents, anti-leaching agents, inert fillers, in particular mineral fillers, anti-freeze agents, stabilisers, dyes, emetic agents, stickers (adhesion promoters), etc.

In particular the formulations may include co-solvents or other solvents. These other solvents or co-solvents are preferably selected from the following group:

linear or branched, saturated or unsaturated, aliphatic hydrocarbons, possibly containing a halogen-, phosphorus-, sulfur- and/or nitrogen atom and/or a functional group, carbocyclic or heterocyclic hydrocarbons, whether saturated, unsaturated or aromatic, possibly containing a halogen-, phosphorus-, sulfur- and/or nitrogen atom and/or a functional group, Even more advantageously, they will be selected from the following group:

alkanes, cycloalkanes and aromatic derivatives, for example paraffins with a branched chain or straight chain such as "white oil" or decalin; mono-, di- or tri alkyl benzenes or naphthalenes, the compounds sold under the trade name Solvesso 100, 150, 200 standard and ND grades;

aliphatic, cycloaliphatic or aromatic mono-, di- or tri-esters, for example alkyl alkanoates such as methyl oleate; benzyl alkanoates; alkyl benzoates; gamma butyrolactone; caprolactone; esters of glycerol and citric acid; alkyl salicylates; phthalates; dibenzoates; acetoacetates; glycol ether acetates, dipropylene glycol diacetate;

alkyl mono-, di-, or tri-phosphates such as for example triethyl phosphate; tributyl phosphate; or tri-2-ethyl-hexylphosphate;

aliphatic, cycloaliphatic or aromatic ketones such as for example dialkyl ketones; benzyl ketones; fenchone; actetophenone; cyclohexanone; alkyl cyclohexanones;

aliphatic, cycloaliphatic or aromatic alcohols such as for example glycols; 2-ethylhexanol; cyclohexanol; benzyl alcohols; tetrahydrofurfuryl alcohol;

aliphatic, cycloaliphatic or aromatic ethers such as for example ethers of glycol, notably ethylene and propylene glycol, and their polymers; diphenyl ether, dipropylene glycol; monomethyl or monobutyl ether, monobutyl ether of tripropylene glycol; alkoxyalkanols; dimethyl isosorbide;

fatty acids such as for example linoleic acid, linolenic acid, oleic acid;

carbonates such as for example propylene or butylene carbonate; lactates; fumarates, succinates, adipates, maleates;

amides such as for example alkyldimethylamides, dimethyl-decanoamide;

alkyl ureas;

amines such as for example alkanolamines, morpholine; N-alkyl-pyrrolidones;

tetramethyl sulfone;

dimethyl sulfoxide;

halogenoalkanes or halogenated aromatic solvents such as for example chloroalkanes or chlorobenzene.

Crystallisation inhibitors may also be present in the formulations. These may be the solvents mentioned here above. They may also be non-polyalkoxylated fatty alcohols or fatty acids, for example mention may be made of the product Alkamuls® OL700 marketed by Rhodia, alkanolamides, polymers etc.

Known conventional methods for preparing phytosanitary formulations or mixtures of solvents may be implemented. It is possible to undertake this by simply mixing the constituents.

The concentrated phytosanitary formulation is generally intended to be spread out over a cultivated field or a field to be cultivated, most often after dilution with water, in order to obtain a diluted composition. Dilution is generally carried out by the farm operator, directly in a tank ("tank-mix"), for example in the tank of a device intended to spread out the composition. This does not exclude the possibility of the farm operator adding other plant protective products, for example fungicides, herbicides, pesticides, insecticides, fertilizers, adjuvants, etc. Thus, the formulation may be used for preparing a composition diluted in water of the active phytosanitary product, by mixing at least one part by weight of concentrated formulation with at least 10 parts of water, preferably less than 10,000 parts. The dilution ratios and the amounts to be applied over the field generally depend on the phytosanitary product and on the desirable dose for treating the field (this may be determined by the farm operator).

EXAMPLES

The following ingredients are used:

Rhodiasolv® Polarclean (Rhodia): Mixture of compounds having the formula (I) with $R^2=R^3=CH_3$ and $R^1=Z-$COOMe- wherein Z is a branched C4 alkylene Rhodiasolv® Iris (Rhodia): Mixture of composition by weight of dimethyl 2-methylglutarate (between 70 and 95%), dimethyl ethyl succinate (between 5% and 30%) and dimethyl adipate (between 0% and 10%): (diester solvent)

Rhodiasolv® ADMA 810 (Rhodia): alkyl dimethylamide solvent (50/50 mixture of compounds with C8 and C10 alkyl chains)

Rhodiasolv® ADMA 10 (Rhodia): alkyl dimethylamide solvent (C10 alkyl chain)

NMP: N-methylpyrrolidone (BASF)

Geronol TEB-25 (Rhodia): mixture of surfactants calcium DBS (Calcium dodecyl benzene sulfonate) and ethoxylated castor oil Geronol TBE-724 (Rhodia): surfactant comprising more than 50% by weight of ethopropoxylated tristyrylphenol Geronol PR-500 (Rhodia): mixture of surfactants based on dodecyl sulfonate and ethoxylated alcohols Rhodacal 60/BE (Rhodia): dodecyl benzene sulfonate based surfactant Antarox B/848 (Rhodia): ethopropoxylated alcohol based surfactant DMP: dimethylphosphate Example 1

Solubility in Water

The solubility limit of the solvent in water is measured by visual observation. If at the studied concentration, the mixture is clear, the solvent is considered to be soluble in water at this concentration. If a certain cloudiness or phase separation is observed then the solvent is considered to be immiscible in water at this concentration. All the measurements are performed at 20° C. to 25° C. and the observations are recorded after stirring for a period of 24 hours in order to allow for equilibration time to be established.

Figure 1:
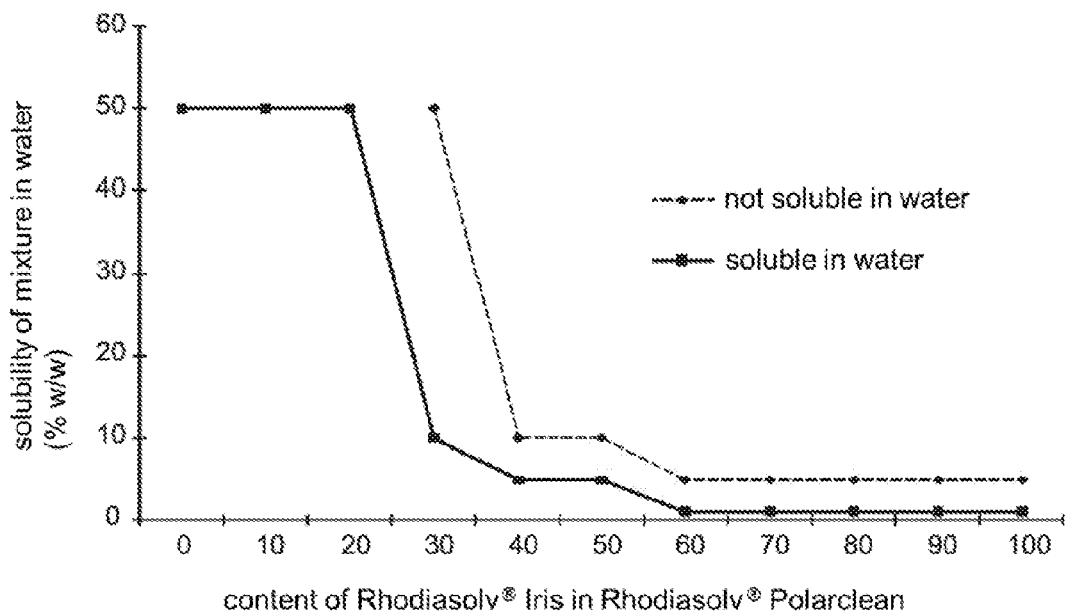
FIG. 1 shows the solubility in water of a composition according to the invention comprising of a mixture of the solvents Rhodiasolv® Polarclean and Rhodiasolv® Iris, with different product content levels for each of these products.

The solubility limits of a mixture of Rhodiasolv® Polarclean/Rhodiasolv® Iris, and of a mixture of Rhodiasolv® Polarclean/ADMA 810 are shown respectively in FIGS. 1 and 2.

Example 2

Solubility of Agrochemical Active Ingredients in the Compositions of the Invention 1. Description of the Tests Performed:

The formulations were prepared by dilution of various active ingredients reported in the table here below in the compositions 1 to 4 (solvents according to the invention) synthesised here above:

a) Visual observation at 25° C.: the appearance of the formulation is noted and the possible presence of crystals is eventually recorded.

b) Visual observation at 0° C.: the formulation is placed for a period of 7 days at 0° C. and the appearance of the formulation is noted and the possible presence of crystals is eventually recorded (CIPAC test MT39).

c) Visual observation at 0° C. with nucleation (for introduction into the liquid of a crystal of the pure active ingredient): A crystal of the active material is introduced into the formulation that has been left for a period of 7 days at 0° C. for nucleation, and then the formulation is once again placed for a period of 7 days at 0° C. The appearance of the formulation is noted and the possible presence of crystals or growth of the crystal introduced is eventually recorded.

The active ingredients used are commercially available. When the formation of crystals of the active ingredient is observed, the term "Crystal" is indicated in the tables here below. In this case, the subsequent test is not carried out and the symbol "-" is reported in the table. When the solution is clear (absence of solid matter or cloudiness), it is the term "Clear" that is reported in the tables of results here below.

2. Results:

The results are recorded in the following tables wherein the solvent mixtures are expressed in volume.

|  | Solvents/no | | | | |
|---|---|---|---|---|---|
|  | 1 | 2 | 3 | 4 (comp) | 5 (comp) |
| Rhodiasolv ® Polarclean (A) | 42 | 53 | 50 | 100 | — |
| ADMA 10 (B) | 28 | 20 | 18 | — | 100 |
| Cyclohexyl acetate (B) | — | — | — | — | — |
| Benzyl acetate (B) | 30 | 27 | 25 | — | — |
| Rhodiasolv ® IRIS (B) | — | — | 7 | — | — |

The table here under indicates the results with the solvents of the above table with a mixture of active ingredients ethofumesate (11%), phenmedipham (PMP) (9%) and DMP (7%) EC.

|  | Solvents | | | | |
|---|---|---|---|---|---|
|  | 1 | 2 | 3 | 4 | 5 |
| State of the solution at +25° C. | Clear | Clear | Slight cloudiness | Slight cloudiness | Slight cloudiness |
| State of the solution at 0° C. | Clear | Clear | Almost clear | Clear with presence of solid (viscous solution) | Clear with presence of solid |
| State of the solution at 0° C. after seeding | Clear | Clear | Clear | Clear with presence of solid (viscous solution) | Clear with presence of solid |

The compositions according to the invention (1, 2 and 3) therefore allow for the solubilisation of the active ingredients mixture in a satisfactory manner, unlike the comparative solvents (4 and 5).

The following mixtures were also prepared.

|  | Solvents/no | | | |
|---|---|---|---|---|
|  | 4 | 5 | 6 | 7 |
| Rhodiasolv ® Polarclean (A) | 100 | — | — | 40 |
| ADMA 10 (B) | — | 100 | — | 60 |
| NMP (A) | — | — | 100 | — |

The table here under indicates the results with the solvents of the above table with tebuconazole 300 g/L EC.

|  | Solvents | | | |
|---|---|---|---|---|
|  | 4 (comp) | 5 (comp) | 6 (comp) | 7 |
| State of the solution at +25° C. | Clear | Clear | Clear | Clear |
| State of the solution at 0° C. | Clear | Clear | Clear | Clear |
| State of the solution at 0° C. after seeding | Crystal | Crystal | Crystal | Clear |

The composition according to the invention (7) therefore allows for the solubilisation of the tebuconazole in a satisfactory manner satisfactorily.

Example 3

Obtaining Emulsification

The complete formulations are evaluated by checking the stability of the emulsions under controlled conditions. The solutions of active ingredients and surfactant systems are dispersed in water solutions of differing hardness (A: ; D: ; C:) and the emulsions formed and stored at controlled temperature are observed after a defined period. The data here under are a compilation of the key findings of this study.

The numerical values in the tables represent the heights (expressed in % volume) of the upper layer in the case of phase separation,
t: cloudiness
cr: formation of crystals (unacceptable in the test)
ol: formation of an oily layer immiscible with water
The following solvents were used:
Composition of Mixtures of Solvents

| Mixture | Mixture 0 (commercial reference) | Mixture 1 (invention) | Mixture 2 (invention) |
|---|---|---|---|
| Rhodiasolv ® Polarclean (A) | — | 40 | 35 |
| ADMA 10 (B) | 100 | 60 | — |
| ADMA 810 (B) | — | — | 65 |
| NMP (A) | — | — | — |

Based on these solvents, or these mixtures, several formulations of phytosanitary active ingredients have been tested and the results are indicated in the tables below.

Formulation 1

The formulation 1 contains by way of phytosanitary active ingredient tebuconazole 250 g/l EC (emulsifier=Geronol TEB-25 at 150 g/l).

The results related to stability of the emulsions obtained with the mixtures 0, 1 and 2 as described here above are indicated in the tables here under.

Stability of the Emulsion at +30° C. (Concentration: 0.5%)

|  | Mixture 0 (commercial reference) | | | Mixture 1 (invention) | | | Mixture 2 (invention) | | |
|---|---|---|---|---|---|---|---|---|---|
| Duration (h) | A | D | C | A | D | C | A | D | C |
| 1 | 0 | 0 | 0 | 0 | 0 | 0 | 0 | 0 | 0 |
| 2 | 0 | 0 | 0 | 0 | 0 | 0 | 0 | 0 | 0 |
| 24 | 1 | 1 | 0 | 0 | 0 | 0 | 0.01 | 0 | 0 |
| | Separation of phase in creamy form | | | | | | | | |

It is thus noted that all the emulsions with tebuconazole and the two mixtures according to the invention are stable at 30° C. for up to 24 hours without phase separation, in contrast to the emulsions with the commercial mixture.

Stability of the Emulsion at +30° C. (Concentration: 5%)

|  | Mixture 0 (commercial reference) | | | Mixture 1 (invention) | | | Mixture 2 (invention) | | |
|---|---|---|---|---|---|---|---|---|---|
| Duration (h) | A | D | C | A | D | C | A | D | C |
| 1 | 0 | 0 | 0 | 0 | 0 | 0 | 0 | 0 | 0 |
| 2 | 0 | 0 | 0 | 0 | 0 | 0 | 0 | 0 | 0 |
| 24 | 1 | 1 | 0 | 0 | 0 | 0 | 0.01 | 0 | 0 |
| | Separation of phase in creamy form | | | | | | | | |

It is thus noted that all the emulsions with tebuconazole and the two mixtures according to the invention are stable at 30° C. for up to 24 hours without phase separation, in contrast to the emulsions with the commercial mixture.

Formulation 2

The formulation 2 contains by way of phytosanitary active ingredient tebuconazole 250 g/l EC (emulsifier=Geronol TEB-25 at 100 g/l).

Stability of the Emulsion at +30° C. (Concentration: 0.5%)

|  | Mixture 0 (commercial reference) | | | Mixture 1 (invention) | | |
|---|---|---|---|---|---|---|
| Duration (h) | A | D | C | A | D | C |
| 1 | 0 | 0 | 0 | 0 | 0 | 0 |
| 2 | 0 | 0 | 0 | 0 | 0 | 0 |
| 24 | 0.5 | 0.5/1 | 2 | 0 | 0 | 0 |
| | Separation of phase in creamy form | | | | | |

It was found that the emulsions with tebuconazole and mixture 1 according to the invention are stable at 30° C. for up to 24 hours without phase separation, in contrast to the emulsions with the commercial mixture.

Formulation 3

The formulation 3 contains by way of phytosanitary active ingredient tebuconazole 300 g/l EC (emulsifier=Geronol TEB-25 at 100 g/l).

Stability of the Emulsion at +30° C. (Concentration: 0.5%)

|  | Mixture 0 (commercial reference) | | | Mixture 1 (invention) | | |
|---|---|---|---|---|---|---|
| Duration (h) | A | D | C | A | D | C |
| 1 | 0 | 0 | 0 | 0 | 0 | 0 |
| 2 | 0 | 0 | 0 | 0 | 0 | 0 |
| 24 | 0.5 | 0.5/1 | 2 | 0 | 0 | 0 |
| | Separation of phase in creamy form | | | | | |

It was found that the emulsions with tebuconazole and mixture 1 according to the invention are stable at 30° C. for up to 24 hours without phase separation, in contrast to the emulsions with the commercial mixture.

Stability of the Emulsion at +54° C. (Concentration: 0.5%)

|  | Mixture 0 (commercial reference) | | | Mixture 1 (invention) | | |
|---|---|---|---|---|---|---|
| Duration (h) | A | D | C | A | D | C |
| 1 | 0 | 0 | 0 | 0 | 0 | 0 |
| 2 | 0 | 0 | 0 | 0 | 0 | 0 |
| 24 | 0.5 | 0.5/1 | 2 | 0 | 0 | 0 |
| | Separation of phase in creamy form | | | | | |

It was found that the emulsions with tebuconazole and mixture 1 according to the invention are stable at 54° C. for up to 24 hours without phase separation, in contrast to the emulsions with the commercial mixture.

Stability of the Emulsion at 0° C. (Concentration: 0.5%)

|  | Mixture 0 (commercial reference) | | | Mixture 1 (invention) | | |
|---|---|---|---|---|---|---|
| Duration (h) | A | D | C | A | D | C |
| 1 | 0 | 0 | 0 | 0 | 0 | 0 |
| 2 | 0 | 0 | 0 | 0 | 0 | 0 |
| 24 | 0.5 | 0.5/1 | 2 | 0 | 0 | 0 |
| | Separation of phase in creamy form | | | | | |

It was found that the emulsions with tebuconazole and mixture 1 according to the invention are stable at 0° C. for up to 24 hours without phase separation, in contrast to the emulsions with the commercial mixture.

Formulation 4

The formulation 4 contains by way of phytosanitary active ingredient a mixture of ethofumesate 11%/phenmedipham 9%/DMP 7% EC (emulsifier=Geronol TBE-724 at 150 g/l).

Stability of the Emulsion at +30° C. (Concentration: 0.5%)

|  | Mixture 0 (commercial reference) | | | Mixture 1 (invention) | | |
|---|---|---|---|---|---|---|
| Duration (h) | A | D | C | A | D | C |
| 1 | 0 | 0 | 0 | 0 | 0 | 0 |
| 2 | 0 | 0 | 0 | 0 | 0 | 0 |
| 4 | 0.5 | 0.5/1 | 2 | 0 | 0 | 0 |
| 24 | | | | 0 | 0 | 0 |
| 24 h 30 min | | | | 0 | 0 | 0 |

It was found that the emulsions with the mixture of active ingredients and mixture 1 according to the invention are more stable at 30° C. than the emulsions with the commercial mixture.

Stability of the Emulsion at +30° C. (Concentration: 5%)

|  | Mixture 0 (commercial reference) | | | Mixture 1 (invention) | | |
| --- | --- | --- | --- | --- | --- | --- |
| Duration (h) | A | D | C | A | D | C |
| 1 | 0 | 0 | 0 | 0 | 0 | 0 |
| 2 | 0 | 0 | 0 | 0 | 0 | 0 |

It was found that the emulsions with the mixture of active ingredients and mixture 1 according to the invention are stable.

The test was replicated after storage of the stock solution for a period of 14 days at +54° C.

Stability of the Emulsion at +30° C. (Concentration: 0.5%)

|  | Mixture 0 (commercial reference) | | | Mixture 1 (invention) | | |
| --- | --- | --- | --- | --- | --- | --- |
| Duration (h) | A | D | C | A | D | C |
| 1 | 0 | 0 | 0 | 0 | 0 | 0 |
| 2 | 0 | 0 | 0 | 0 | 0 | 0 |
| 4 | 0.5 | 0.5/1 | 2 | 0 | 0 | 0 |
| 24 |  |  |  | 0 | 0 | 0 |
| 24 h 30 min |  |  |  | 0 | 0 | 0 |

It was found that the emulsions with the mixture of active ingredients and mixture 1 according to the invention are stable, and notably more stable than those obtained with the commercial mixture.

Stability of the Emulsion at +30° C. (Concentration: 5%)

|  | Mixture 0 (commercial reference) | | | Mixture 1 (invention) | | |
| --- | --- | --- | --- | --- | --- | --- |
| Duration (h) | A | D | C | A | D | C |
| 1 | 0 | 0 | 0 | 0 | 0 | 0 |
| 2 | 0 | 0 | 0 | 0 | 0 | 0 |

It was found that the emulsions with the mixture of active ingredients and mixture 1 according to the invention are stable.

Formulation 5

The formulation 5 contains by way of phytosanitary active ingredient a mixture of phenmedipham 13%/DMP 4% EC (emulsifier=Geronol TBE-724 at 150 g/l).

Stability of the Emulsion at +30° C. (Concentration: 0.5%)

|  | Mixture 0 (commercial reference) | | | Mixture 1 (invention) | | |
| --- | --- | --- | --- | --- | --- | --- |
| Duration (h) | A | D | C | A | D | C |
| 1 | 0 | 0 | 0 | 0 | 0 | 0 |
| 2 | 0 | 0 | 0 | 0 | 0 | 0 |
| 4 | 0.5 | 0.5/1 | 2 | 0 | 0 | 0 |
| 24 |  |  |  | 0 | 0 | 0 |
| 24 h 30 min |  |  |  | 0 | 0 | 0 |

It was found that the emulsions with the mixture of active ingredients and mixture 1 according to the invention are stable.

Stability of the Emulsion at +30° C. (Concentration: 5%)

|  | Mixture 0 (commercial reference) | | | Mixture 1 (invention) | | |
| --- | --- | --- | --- | --- | --- | --- |
| Duration (h) | A | D | C | A | D | C |
| 1 | 0 | 0 | 0 | 0 | 0 | 0 |
| 2 | 0 | 0 | 0 | 0 | 0 | 0 |

It was found that the emulsions with the mixture of active ingredients and mixture 1 according to the invention are stable.

Example 4

Preparation of Compositions According to the Invention

The following compositions were prepared by mixing the solvents in the proportions as indicated here under.

| Example | Rhodiasolv ® Polarclean | ADMA 10 | Diester Rhodiasolv ® RPDE | Fatty acid methyl ester (Canola methyl ester) | Hansen Solubility Parameters $\delta_D$ ($(J/cm^3)^{1/2}$) | $\delta_P$ ($(J/cm^3)^{1/2}$) | $\delta_H$ ($(J/cm^3)^{1/2}$) |
| --- | --- | --- | --- | --- | --- | --- | --- |
| 4.0 | 100 | 0 | 0 | 0 | 15.8 | 10.7 | 9.2 |
| 4.1 | 52.2% | 34% | 0% | 13.8% | 15.9 | 8.3 | 7.8 |
| 4.2 | 60% | 40% | 0% | 0% | 16.1 | 8.98 | 8.5 |
| 4.3 | 30% | 50% | 20% | 0% | 16.3 | 8.5 | 8.6 |

Example 4.0 corresponds to comparative mixture 4 of Example 2.

Example 5

Solubilisation of Active Ingredients by the Mixtures of Example 4

The following emulsifiable concentrates were prepared using the mixtures shown in Example 4.

It was observed that the compositions thus obtained were stable and showed good emulsion stability.

Example 5.1

Formulation with Propanil 360 g/L

| Propanil Tech. 98% | 367 g/L |
| Mixture shown in Example 4.1 | 538 g/L |
| Geronol PR-500 | 170 g/L |

Example 5.2

Formulation with Cypermethrin 20%

| Cypermethrin Tech. 94.6% | 21.2 g/L |
| Mixture 7 shown in Example 2 | 68.8 g/L |
| Geronol TBE-724 | 10.0 g/L |

Example 5.3

Formulation with Oxyfluorfen 23%

| Oxyfluorfen Tech. 95% | 24.2 g/L |
| Mixture 7 shown in Example 2 | 65.8 g/L |
| Geronol TBE-724 | 10.0 g/L |

Example 5.4

Formulation with Prochloraz 450 g/L

| Prochloraz tech. 96.9% | 464 g/L |
| Mixture shown in Example 4.2 | 564 g/L |
| Rhodacal 60/BE | 24 g/L |
| Antarox B/848 | 56 g/L |

It was found that all of these EC (emulsifiable concentrates) compositions have low viscosity and generate no crystallisation of the active ingredient at 0° C. for at least 1 month.

The emulsification stability tests were carried out according to the CIPAC (Collaborative International Pesticides Analytical Council) Method MT 36 and the results are in conformity with the requirements of the phytosanitary industry.

Example 6

Preparation of Formulations with the Mixture of Example 4.3

The formulations in the form of emulsifiable concentrates were prepared using various agrochemical active ingredients.

| Active ingredients | Concentration of Active ingredients |
|---|---|
| Abamectin | 18 g/l |
| Flufenoxuron | 100 g/l |
| Lufenuron | 50 g/l |
| Oxyfluorfen | 240 g/l |
| Propanil | 360 g/l |
| Prochloraz | 450 g/l |
| Uniconazole | 50 g/l |
| Cyfluthrin | 100 g/l |
| Bromoxynil | 350 g/l |
| Ethofenprox | 30% |
| Myclobutanil | 200 g/l |
| Ethofumesate-PMP-DMP | 11%-9%-7% |

Thus, the mixture shown in Example 4.3. provides for the solubilisation of a large number of active ingredients, most of which are usually solubilised in toxic solvents such as isophorone, cyclohexanone or NMP.

It was found that all of these EC (emulsifiable concentrates) compositions have low viscosity and generate no crystallisation of the active ingredient at 0° C. for at least 1 month.

The emulsification stability tests were carried out according to the CIPAC (Collaborative International Pesticides Analytical Council) Method MT 36 and the results are in conformity with the requirements of the phytosanitary industry.

The invention claimed is:

1. A composition comprising:
from 10% to 90% by weight of a mixture M of compounds A having the formula (I):

$$R^1 CONR^2 R^3 \qquad (I)$$

the said mixture comprising at least two compounds A having different formulas (I), wherein:
$R^1$ is a group having the formula —Z—COOR', where Z is a linear or branched divalent alkylene group comprising from 2 to 4 carbon atoms and R' is a methyl group;
$R^2$ and $R^3$, which are identical or different, are methyl or ethyl groups; and
from 10% to 90% by weight of at least one compound B selected from amide solvents, optionally in combination with an ester solvent.

2. A composition according to claim 1, in which the mixture M is a mixture of compounds having the formula (I), the mixture comprising:
a compound having the formula (I) wherein $R^1$ is —CH(CH$_2$—CH$_3$)—CH$_2$—COOMe,
a compound having the formula (I) wherein $R^1$ is —CH$_2$—CH(CH$_2$—CH$_3$)—COOMe
a compound having the formula (I) wherein $R^1$ is —CH(CH$_3$)—CH$_2$—CH$_2$—COOMe, and
a compound having the formula (I) wherein $R^1$ is —CH$_2$—CH$_2$—CH(CH$_3$)—COOMe.

3. A composition according to claim 2, in which the mixture M further comprises a compound having the formula (I) wherein $R^1$ is —(CH$_2$)$_4$—COOMe.

4. A composition according to claim 1, in which the mixture M comprises at least one compound A having the formula (I) wherein $R^2$ and $R^3$ are methyl groups.

5. A composition according to claim 1, that comprises at least one amide solvent as compound B in a mixture with at least one ester solvent.

6. A composition according to claim 1, in which the amide solvents are chosen from compounds having the formula (II):

R"—CONMe₂     (II)

where R" is a linear or branched alkyl group, comprising of 8 to 20 carbon atoms.

7. A composition according to claim 6, in which the amide solvents are chosen from the compounds having the formula (II) wherein R" is selected from among the C8, C10, C12, C18 linear alkyls and mixtures thereof, in all ratios.

8. A composition according to claim 1, in which the ester solvent is selected from the group consisting of 2-ethylhexyl lactate, alkyl acetates, esters of fatty acids, fatty esters of carboxylic acids and mixtures of methyl diesters of 2-ethyl succinic acid, methylglutaric acid and optionally adipic acid.

9. A composition according to claim 1, comprising:
from 20% to 60% by weight of the mixture M, and
from 40% to 80% by weight of the compound B,
wherein the mixture M is a mixture of compounds having the formula (I), the mixture comprising:
a compound having the formula (I) wherein $R^1$ is —CH(CH₂—CH₃)—CH₂—COOMe,
a compound having the formula (I) wherein $R^1$ is —CH₂—CH(CH₂—CH₃)—COOMe
a compound having the formula (I) wherein $R^1$ is —CH(CH₃)—CH₂—CH₂—COOMe, and
a compound having the formula (I) wherein $R^1$ is —CH₂—CH₂—CH(CH₃)—COOMe; and
wherein compound B is selected from amide solvents, optionally in combination with an ester solvent.

10. A method for obtaining a composition of solvents having a water solubility of less than or equal to 1% by weight at 20° C.-25° C., the method comprising mixing from 10% to 90% by weight of at least one mixture M with 10% to 90% by weight of at least one compound B;
wherein the mixture M is a mixture of compounds A having the formula (I):

R¹CONR²R³     (I)

the said mixture comprising at least two compounds A having different formulas (I), wherein:
$R^1$ is a group having the formula —Z—COOR', where Z is a linear or branched divalent alkylene group comprising from 2 to 4 carbon atoms and R' is a methyl group;
$R^2$ and $R^3$, which are identical or different, are methyl or ethyl groups; and
wherein compound B is selected from amide solvents, optionally in combination with an ester solvent.

11. A solvent having a water solubility of less than or equal to 1% by weight at 20° C.-25° C. comprising the composition according to claim 1.

12. A phytosanitary formulation comprising at least one phytosanitary active ingredient and, as a solvent for the at least one phytosanitary active ingredient, the composition according to claim 1.

13. A phytosanitary formulation according to claim 12, wherein the phytosanitary formulation is in the form of an emulsifiable concentrate, a concentrated emulsion or a micro emulsion.

14. A phytosanitary formulation according to claim 12, in which the phytosanitary active ingredient is selected from among the following compounds:
Abamectin,
Alachlor
Bromoxynil
Chlorpyrifos,
Alpha-cypermethrin,
Cyfluthrin,
Ethofenprox,
Flufenoxuron,
Lufenuron,
Myclobutanil,
Phenmedipham,
Prochloraz,
Propanil,
Pendimethalin,
Azoles,
Triadimenol,
Trifluralin,
Oxyfluorfen,
Imidacloprid,
Ethofumesate,
Dimethyl phosphate,
Dimethoate, and
Propoxur; and mixtures thereof.

15. A phytosanitary formulation according to claim 12, wherein the solvent is from 10% to 90% by weight relative to the weight of the formulation.

16. A phytosanitary formulation according to claim 14, wherein the azole is a triazole.

17. A phytosanitary formulation according to claim 16, wherein the triazole is tebuconazole or uniconazole.

* * * * *